(12) United States Patent  
Murata

(10) Patent No.: US 8,166,835 B2  
(45) Date of Patent: May 1, 2012

(54) SENSOR CHIP AND INSPECTION DEVICE

(75) Inventor: Michiaki Murata, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 122 days.

(21) Appl. No.: 12/076,499

(22) Filed: Mar. 19, 2008

(65) Prior Publication Data

US 2008/0250883 A1 Oct. 16, 2008

(30) Foreign Application Priority Data

Apr. 12, 2007 (JP) ................................. 2007-104665

(51) Int. Cl.
*G01M 99/00* (2006.01)
(52) U.S. Cl. ........................................ 73/865.8; 257/253
(58) Field of Classification Search .................. 73/865.8
See application file for complete search history.

(56) References Cited

U.S. PATENT DOCUMENTS

| | | | | |
|---|---|---|---|---|
| 4,611,223 A * | 9/1986 | Hine et al. | ..................... | 257/446 |
| 5,189,914 A * | 3/1993 | White et al. | ..................... | 73/599 |
| 6,060,023 A * | 5/2000 | Maracas | ..................... | 422/68.1 |
| 6,140,144 A * | 10/2000 | Najafi et al. | ..................... | 438/53 |
| 6,485,690 B1 * | 11/2002 | Pfost et al. | ..................... | 422/102 |
| 2002/0033335 A1 | 3/2002 | Terashima et al. | | |
| 2002/0105368 A1 * | 8/2002 | Morishita | ..................... | 327/310 |
| 2004/0126279 A1 * | 7/2004 | Renzi et al. | ..................... | 422/100 |
| 2004/0129947 A1 * | 7/2004 | Miyashita | ..................... | 257/99 |
| 2004/0214240 A1 * | 10/2004 | Cao | ..................... | 435/7.2 |
| 2004/0242982 A1 | 12/2004 | Sakata et al. | | |
| 2006/0159590 A1 * | 7/2006 | Pechstein et al. | ..................... | 422/88 |
| 2006/0229502 A1 | 10/2006 | Pollock et al. | | |
| 2007/0025877 A1 | 2/2007 | Hansen | | |
| 2007/0117253 A1 * | 5/2007 | Hsu et al. | ..................... | 438/75 |
| 2008/0061323 A1 * | 3/2008 | Yazawa et al. | ..................... | 257/253 |
| 2008/0105566 A1 | 5/2008 | Kitawaki et al. | | |
| 2008/0227235 A1 * | 9/2008 | Theuss et al. | ..................... | 438/53 |
| 2008/0283875 A1 | 11/2008 | Mukasa et al. | | |

FOREIGN PATENT DOCUMENTS

| | | |
|---|---|---|
| JP | A-1-105155 | 4/1989 |
| JP | A-64-91052 | 4/1989 |
| JP | A-02-220375 | 9/1990 |
| JP | A-2002-39990 | 2/2002 |
| JP | A 2004-110909 | 4/2004 |
| JP | A 2005-274574 | 10/2005 |
| JP | A 2005-300213 | 10/2005 |
| JP | A 2005-534004 | 11/2005 |
| JP | A-2005-345464 | 12/2005 |
| WO | WO 03/025559 A1 | 3/2003 |
| WO | WO 2004-010537 A2 | 1/2004 |
| WO | WO 2005/000114 A2 | 1/2005 |
| WO | WO 2006/134942 A1 | 12/2006 |

OTHER PUBLICATIONS

Aug. 9, 2011 Office Action issued in Japanese Patent Application No. 2007-104665 (with translation).
Jan. 24, 2012 Japanese Office Action issued in Japanese Patent Application No. 2007-104665 (with translation).

* cited by examiner

*Primary Examiner* — Hezron E Williams
*Assistant Examiner* — Nashmiya Fayyaz
(74) *Attorney, Agent, or Firm* — Oliff & Berridge, PLC

(57) ABSTRACT

A sensor chip of an electrical signal detection type, comprises a semiconductor sensing device, the sensor chip being detachable with respect to an inspection device.

16 Claims, 15 Drawing Sheets

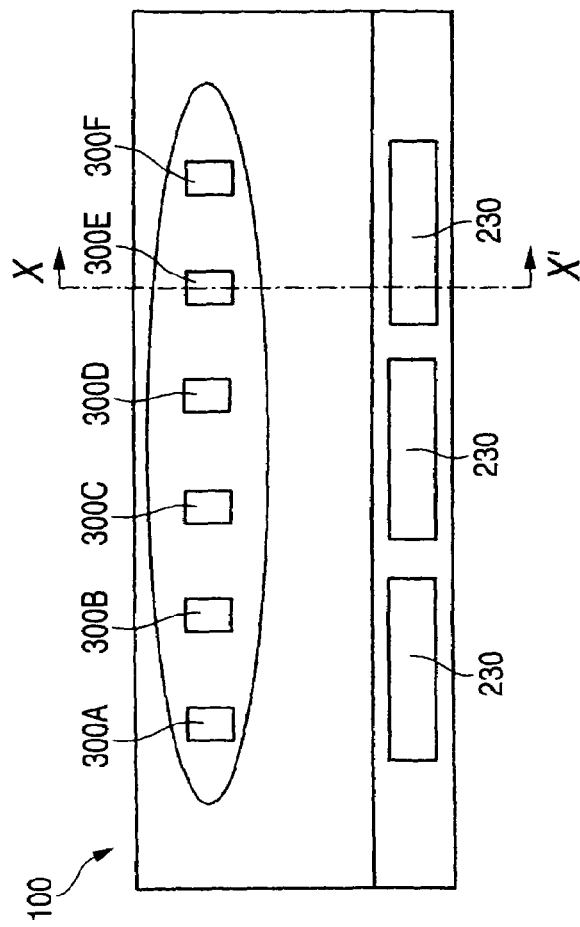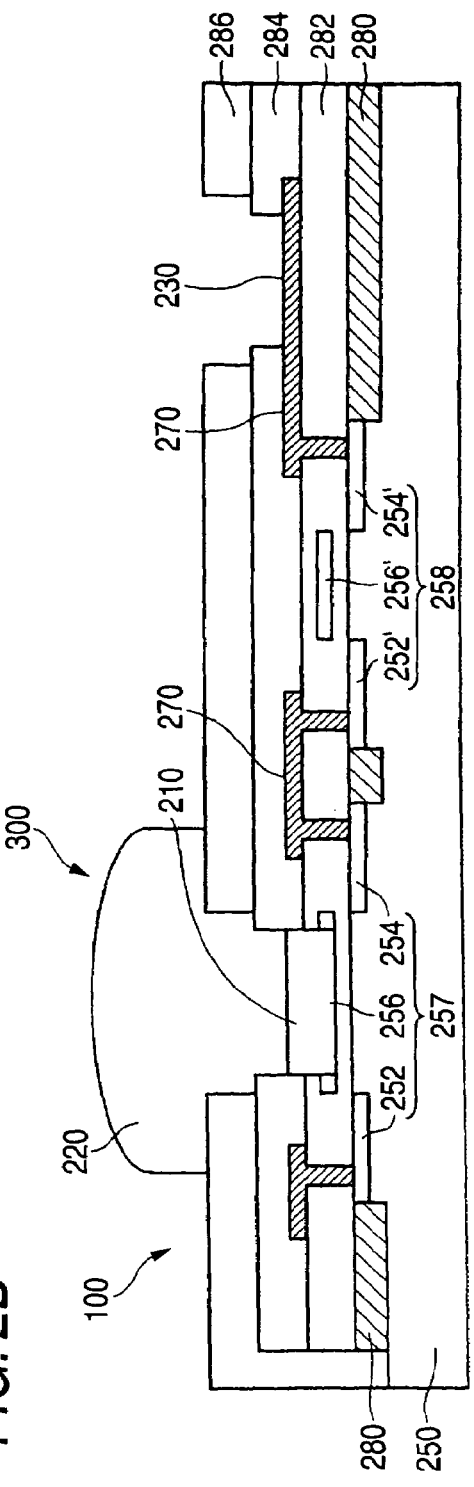
FIG. 2A
FIG. 2B

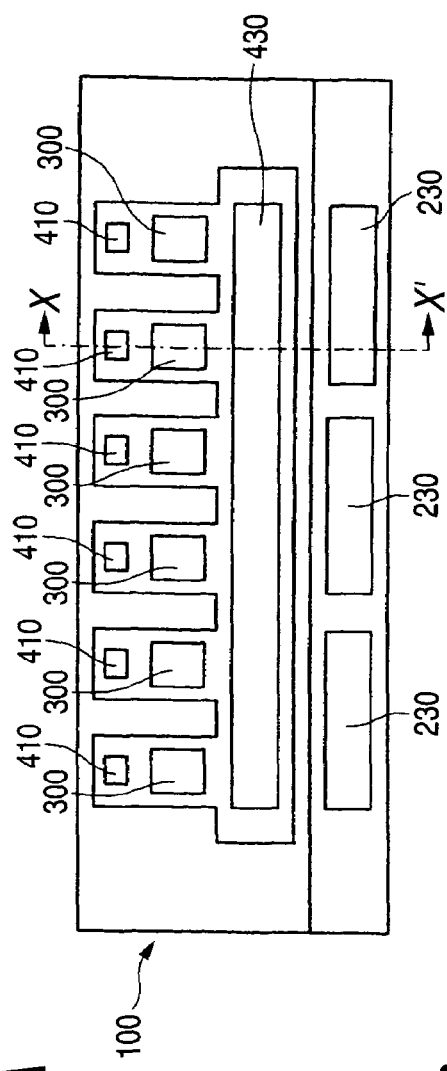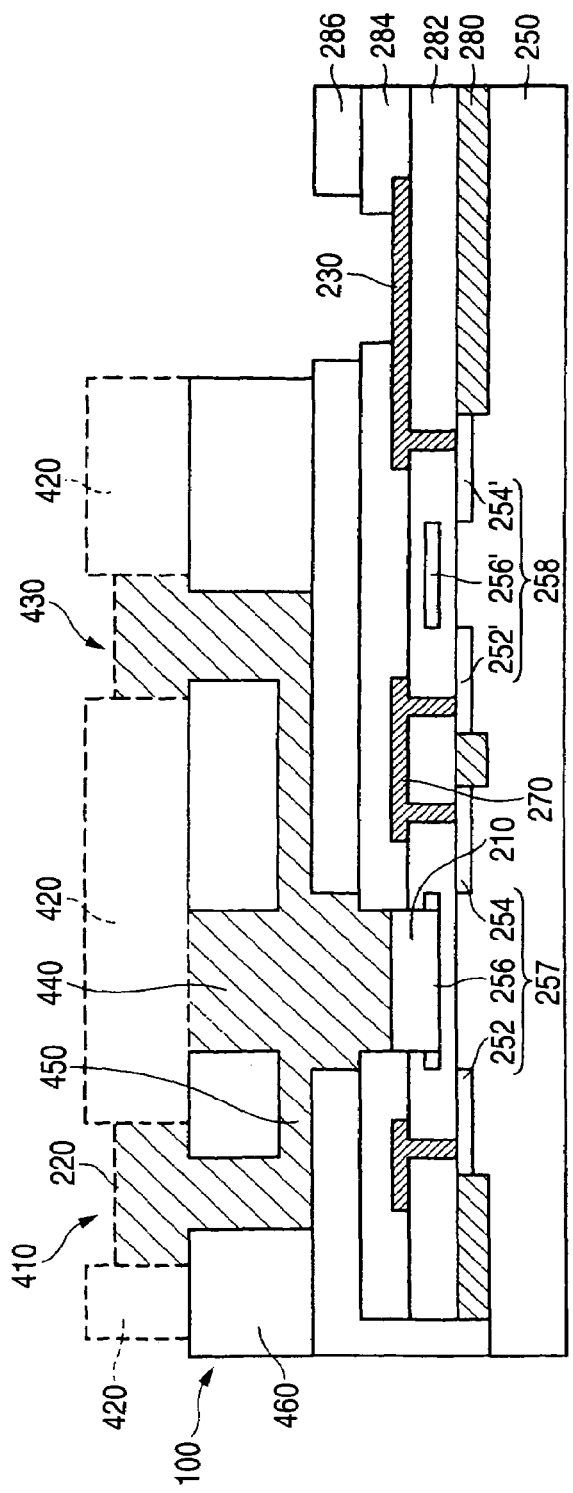
FIG. 4A
FIG. 4B

SENSOR CHIP AND INSPECTION DEVICE

CROSS-REFERENCE TO RELATED APPLICATIONS

This application is based on and claims priority under 35 USC 119 from Japanese Patent Application No. 2007-104665 filed Apr. 12, 2007.

BACKGROUND (i) Technical Field

The present invention relates to a sensor chip and an inspection device.

(ii) Related Art

In recent years, biosensors and chemical sensors have come to be used in such as medical checkups gene analyses. As for these biosensors and chemical sensors, there are an optical detection method and an electrical signal detection method.

The electrical signal detection method is a method in which analysis of a substance to be measured (e.g., blood) is carried out by electrodes and a semiconductor device formed on a chip. The electrical signal detection method has a characteristic that inspection can be performed simply in a short time, and it is expected that the inspection can be carried out not only at hospitals but clinics and even at homes or the like.

SUMMARY

According to an aspect of the invention, there is provided a sensor chip of an electrical signal detection type, comprising a semiconductor sensing device, the sensor chip being detachable with respect to an inspection device.

BRIEF DESCRIPTION OF THE DRAWINGS

Exemplary embodiments of the present invention will be described in detail based on the following figure, wherein:

FIG. 2A is a plan view of the sensor chip in accordance with a first exemplary embodiment of the invention;

FIG. 2B is a cross-sectional view taken along line X-X' in the plan view of FIG. 2A;

FIG. 4A is a plan view of the sensor chip in accordance with a second exemplary embodiment of the invention;

FIG. 4B is a cross-sectional view taken along line X-X' in the plan view of FIG. 4A;

DETAILED DESCRIPTION

Figure 1:
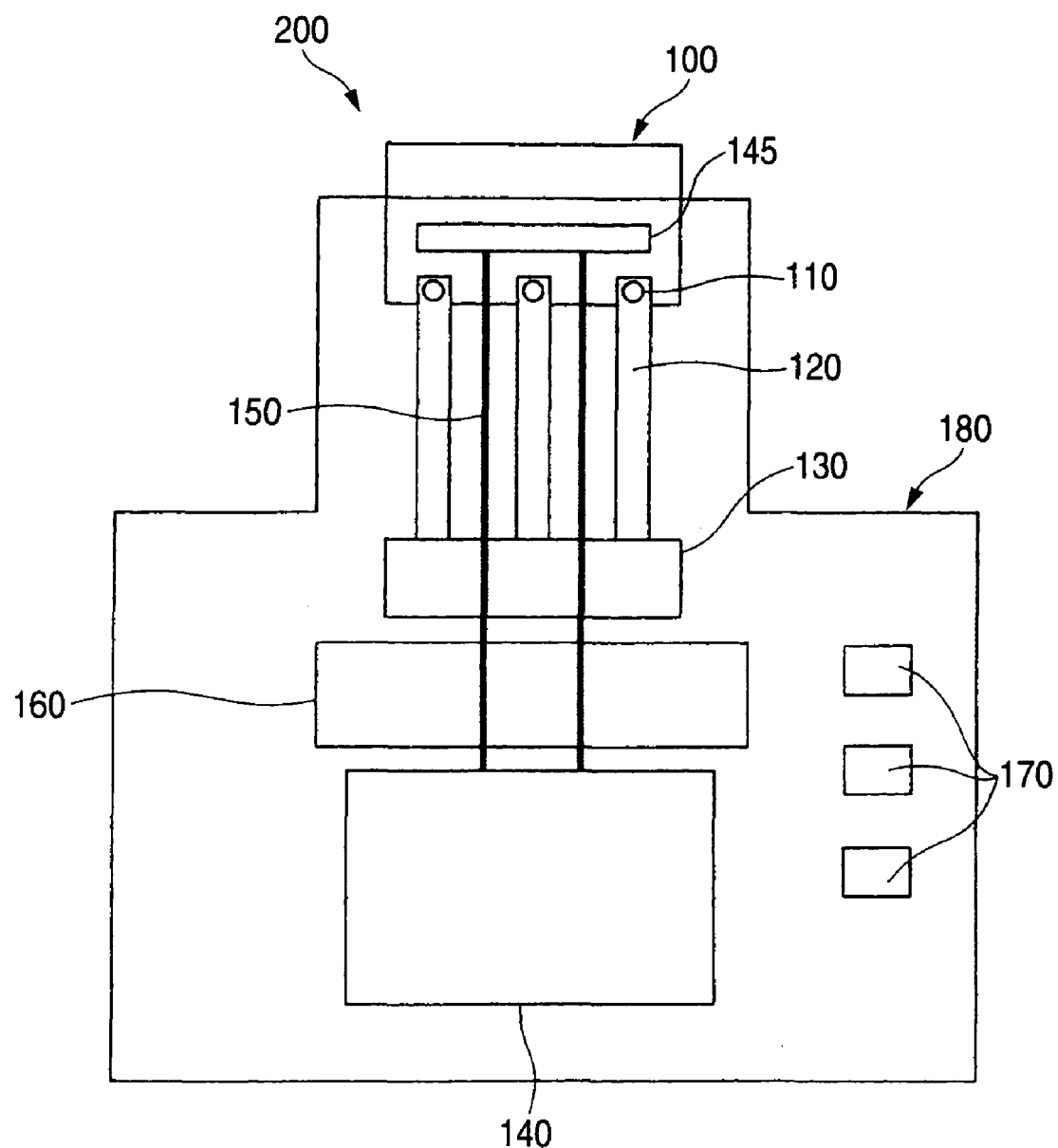
FIG. 1 is a diagram illustrating the configuration of an inspection device having a sensor chip in accordance with one mode for carrying out the invention.

The sensor chip in accordance with the invention is detachable with respect to an inspection device and is a sensor chip of an electrical signal detection type on which a semiconductor sensing device is mounted.

The sensor chip in accordance with the invention is expected to realize the miniaturization of the sensor chip since it has a semiconductor sensing device mounted thereon.

Hereafter, a description will be given of the exemplary embodiments of the invention with reference to the accompanying drawings. It should be noted that, in the drawings, similar constituent elements are denoted by the same reference numerals. In addition, redundant explanations are omitted.

FIG. 1 shows the configuration of an inspection device 200 having the sensor chip in accordance with one mode for carrying out the invention. A sensor chip 100 is detachable with respect to an inspection device body (substrate) 180. It should be noted that the inspection device 200 in accordance with the invention is comprised of the inspection device body (substrate) 180 and the sensor chip 100.

The sensor chip in accordance with the invention can be used as a biosensor chip or a chemical sensor chip, and can be utilized in the inspection of a biological component, a chemical component, and the like.

An output signal from this sensor chip 100 is transmitted through an electrical connection portion 110 and an electrical connection line 120 to an arithmetic circuit 130 where signal analysis is carried out, and its result is displayed on a display 160. A specimen (a liquid to be inspected) (not shown) is introduced into the sensor chip 100 by means of a suction unit 140 provided on the inspection device body (substrate) 180. In addition, the inspection device 200 shown in FIG. 1 is provided with a switch 170 (e.g., designating means for designating operations, such as "on" and "off"). The inspection device 200 is provided with a suction portion 145 and a suction path 150 which are connecting portions between the suction unit 140 and the sensor chip 100 which are disposed on the inspection device body (substrate) 180.

As the inspection device is made compact, as shown in FIG. 1, the inspection device can be expected to be used for in-home inspection and as a portable inspection device.

It should be noted that the suction portion 145, the suction path 150, and the suction unit 140 are arbitrary, and the suction portion and the suction unit are not provided on the sensor chip and the inspection device shown in FIG. 2A to FIG. 3D, as will be described later. In addition, the specimen can be introduced onto the sensor chip without being sucked but by applying pressure at the time of the introduction.

Further, the display 160 and the switch 170 may be provided arbitrarily, and the inspection result may be presented by audio or by a printer or the like insofar as the inspection result can be ascertained by the person being analyzed.

FIG. 2A is a plan view of the sensor chip 100 in accordance with a first exemplary embodiment of the invention, and FIG. 2B is a cross-sectional view taken along line X-X' in the plan view of FIG. 2A.

The sensor chip 100 in accordance with the invention is a sensor chip of the electrical signal detection type on which a semiconductor sensing device is mounted. In FIGS. 2A and 2B, an ion sensitive field effect transistor (ISFET) is provided as the semiconductor sensing device. In addition, in FIGS. 2A and 2B, the sensor chip 100 includes sensor portions 300 and electrical connection pads 230.

The sensor portion 300 consists of a sensing transistor 257 which is an ion sensitive field effect transistor (ISFET) having a source 252 and a drain 254, as well as a receptor 210 disposed at a gate 256 of the sensing transistor 257.

A material corresponding to the substance to be detected is used as the receptor 210, and insofar as the material, upon contact (reaction) with the receptor, causes a change in the surface charge, the receptor 210 is sufficient, and is not particularly limited. In the sensor chip 100 shown in FIGS. 2A and 2B, as the ISFET allows an electric current corresponding to its charge to flow, it is possible to measure (inspect) the presence or absence or the amount of substance. In addition, by changing the kind of the receptor, the sensor chip 100 can be used in the analysis of various substances. It should be noted that, in the invention, an ISFET can be suitably used as the semiconductor sensing device, but the invention is not limited to the same.

The surface of the sensor portion 300 which opposes the receptor 210 should preferably have an opening. The opening is preferably a receptor introducing port, and if the opening is provided as the receptor introducing port, the receptor can be suitably imparted at an arbitrary timing after fabrication of the sensor chip. A description will be given later of the details.

In FIG. 2B, blood is introduced onto the sensor portion 300 as a specimen 220. In the present invention, the sensor chip is preferably provided with a plurality of sensor portions, and six sensor portions 300A to 300F are provided, as shown in FIG. 2A. As different receptors can be respectively disposed on the sensor portions 300A to 300F in FIG. 2A, inspection of a plurality of items can be carried out in one analysis. In addition, when the sensor chip 100 is used for a medical checkup or the like, tailor-made inspection is made possible by changing the receptor to one corresponding to each individual person.

The sensor chip 100 is provided with a switching circuit for designating the ISFET used for the analysis as well as an integrated circuit (e.g., constituted by a metal oxide semiconductor (MOSFET) FET) including a circuit for processing the signal of the ISFET. In FIG. 2B, a MOS transistor 258 consisting of a source 252', a drain 254', and a gate 256' is provided. Further, the electrical connection pads 230 for transmitting and receiving signals to and from the inspection device body (substrate) is provided. It should be noted that the sensing transistor 257 and the MOS transistor 258 are separated by an inter-element separation film 280. In addition, a wiring 270 is provided on the sensor chip.

In FIG. 2B, a polyimide film 286 is provided as an uppermost layer of the sensor chip 100.

The polyimide film 286 is used for ensuring the sealing performance of a seal member at the time of sealing the electrical connection portion 110 between the sensor chip and the inspection device body (see FIGS. 3A to 3D which will be referred to later) Since the polyimide film is flexible and excels in flatness, the polyimide film can be suitably used. It should be noted that in the invention the film may be formed by using other material excelling in flexibility and flatness instead of the polyimide film.

For the details of the configuration of the sensor chip 100, a known ISFET can be referred to, and the sensor chip 100 shown in FIG. 2B has on a substrate 250 the inter-element separation film 280, an interlayer separation film 282, a protective film 284, and the polyimide film 286.

FIGS. 3A to 3D show the configuration of the inspection device 200 using the sensor chip 100 in accordance with the first exemplary embodiment shown in FIGS. 2A and 2B. FIGS. 3A to 3D show a connecting portion between the sensor chip 100 and the inspection device body 180.

Figure 3A:
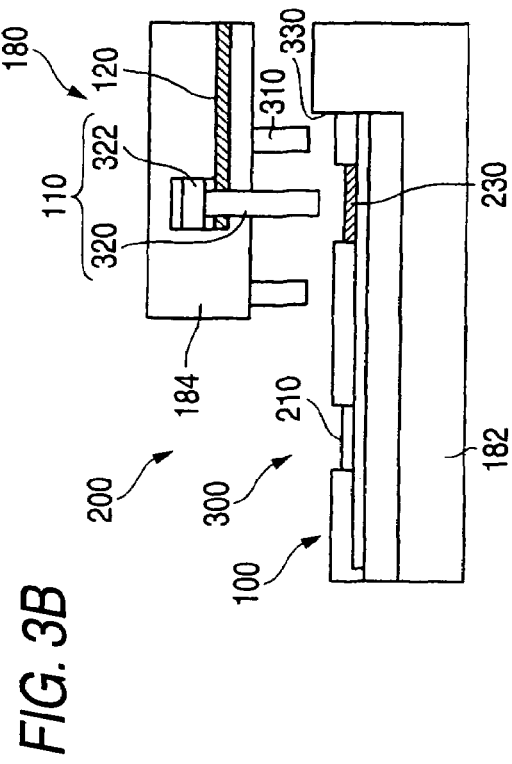
FIGS. 3A to 3D are schematic diagrams illustrating the configuration of the inspection device using the sensor chip in accordance with the first exemplary embodiment shown in FIGS. 2A and 2B.

A datum (step) 330 for alignment with the sensor chip 100 is provided on the inspection device body (substrate) 180 shown in FIG. 3A. The inspection device body 180 should preferably be provided with a member for alignment with the sensor chip, and the datum (step) 330 is provided in FIGS. 3A to 3D, but the invention is not limited to the same. For instance, alignment may be effected by providing a protruding portion on the inspection device body and a recessed portion on the sensor chip and by fitting them together, or alignment may also be effected by providing, conversely, a recessed portion on the inspection device body and a protruding portion on the sensor chip.

The inspection device body electrically connects the sensor chip and the arithmetic circuit provided on the inspection device body. A probe for electrically connecting to the sensor chip is preferably provided on the inspection device body.

In FIG. 3A, a probe pin 320 for electrically connecting to the electrical connection pad 230 disposed on the sensor chip 100 is provided on an upper support 184.

The probe should preferably have a resilient function, and should more preferably have the function of resiliency (i.e., is resilient) in the direction of pressing against the electrical connection pad. In the probe pin 320 shown in FIG. 3A, a spring 322 is provided at an upper portion.

It should be noted that although in FIGS. 3A to 3D the spring is provided for imparting the resilient function to the probe, the invention is not limited to the same, and an elastic body such as rubber may be used for the probe.

Figure 3B:
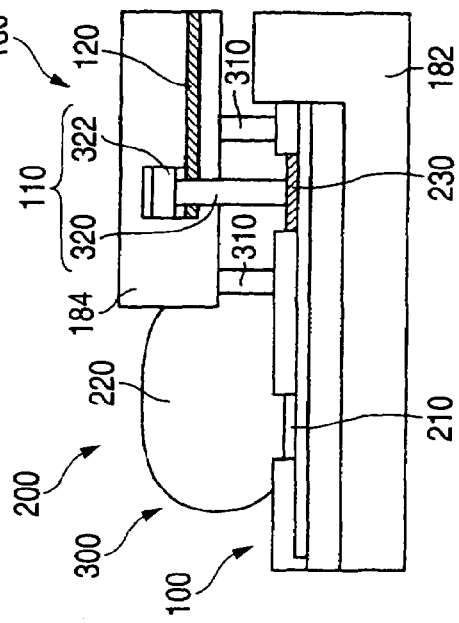

In FIG. 3B, as the sensor chip 100 is abutted against the datum (step for alignment) 330 provided on a lower support 182, alignment is made between the movable probe pin 32 provided on the upper support 184 of the inspection device body (substrate) 180 and the electrical connection pad 230 provided on the sensor chip 100. In the alignment based on this abutment, it is preferred that the electrical connection pad 230 be made sufficiently large so that the positions of the electrical connection pad 230 and the probe pin 320 will not be offset from each other.

At this time, the alignment between a seal member 310 (rubber seal) provided on the upper support 184 and the sensor chip 100 is also completed simultaneously.

Figure 3C:
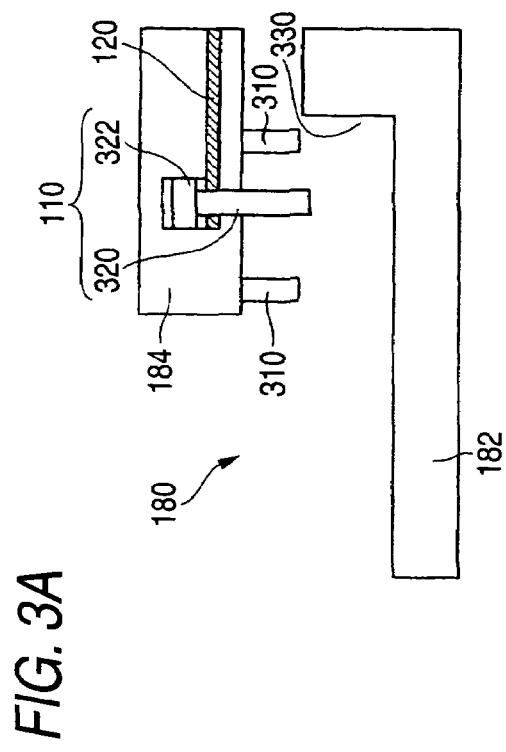

As shown in FIG. 3C, after the mounting of the sensor chip 100, as the upper support 184 is lowered toward the sensor chip 100 side, the electrical connection and the sealing between the specimen and the electrical connection portion are completed simultaneously. Even if the height of the sensor chip 100 and the height of the seal member 310 (rubber seal) slightly vary due to the spring provided in the rear of the probe pin 320, it is possible to ensure the electrical connection (contact).

Figure 3D:
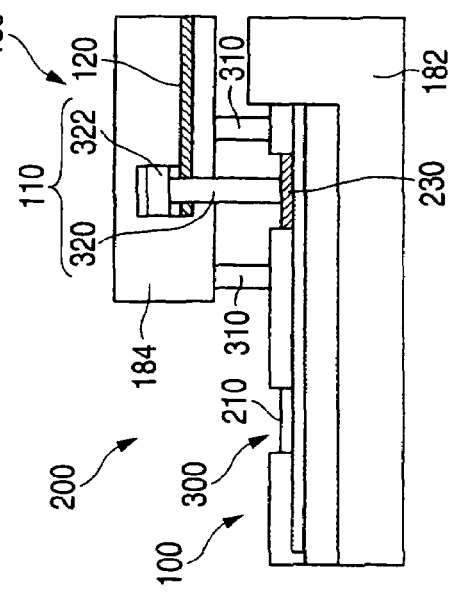

FIG. 3D shows the inspection device 200 with the specimen 220 imparted thereto.

Since the seal member is flexible, as the seal member is pressed, it is possible to ensure isolation between the specimen and the electrical connection portion. Further, as shown in FIG. 2B, as the flexible polyimide film is formed on top of the sensor chip, the sealing performance with respect to the seal member is further enhanced.

It should be noted that, in FIGS. 3A and 3B, the sensor chip 100 is shown in a rough configuration, and only the sensor portion 300, the receptor 210, and the electrical connection pad 230 are shown in FIG. 3B.

In addition, the upper portion and the lower portion of the inspection device body (substrate) are not limited to the same, and the upper and lower sides of the inspection device can be disposed inversely, or on the left- and right-hand sides, and the invention is not limited to the description of the exemplary embodiments.

FIG. 4A is a plan view of the sensor chip 100 in accordance with a second exemplary embodiment of the invention, and FIG. 4B is a cross-sectional view taken along line X-X' in the plan view of FIG. 4A. The difference with the first exemplary embodiment lies in that a channel substrate 460 is provided on the sensor chip 100. As the channel substrate 460, it is possible to cite by way of example a silicon (Si) channel substrate. The channel substrate 460 is joined to the sensor chip, and the specimen to be analyzed passes through a channel 450 and is introduced onto the sensor portion 300. The specimen is preferably in a state of being capable of being fed in the form of a current, and is more preferably a liquid.

The channel substrate 460 is provided with a specimen introducing port 410 which is an opening for introducing the specimen 220, as well as a specimen suction port 430 which is an opening for sucking the specimen. As the specimen 220 is sucked through the specimen suction port 430, the specimen 220 at the specimen introducing port 410 flows into the channel 450 and reaches the sensor portion 300. At this time, the opening 440 which can also be used as a receptor introducing port is sealed by a seal member 420 provided on the upper support.

In addition, in FIG. 4B, the surface of the channel substrate 460 which opposes the receptor 210 should preferably have the opening 440. Preferably, the opening 440 is a receptor introducing port, and if the opening 440 is provided as the receptor introducing port, the receptor can be imparted at an arbitrary timing after fabrication of the sensor chip. Accordingly, tailor-made inspection is made possible as the receptors can be respectively formed on the plurality of sensor portions in correspondence with items of inspection.

FIGS. 5A to 5D show the configuration of the inspection device 200 using the sensor chip 100 in accordance with the second exemplary embodiment. A description of portions having the same construction as those of the first exemplary embodiment will be omitted.

Figure 5A:
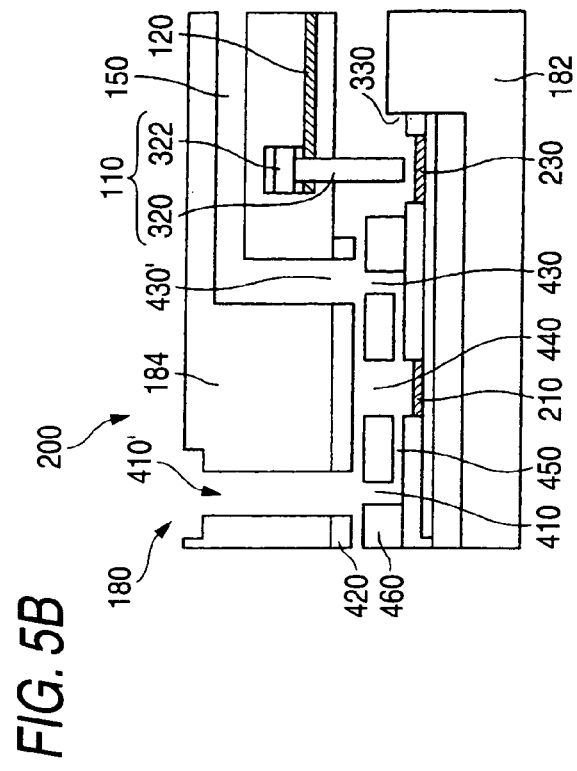
FIGS. 5A to 5D are schematic diagrams illustrating the configuration of the inspection device using the sensor chip in accordance with the second exemplary embodiment.

As shown in FIG. 5A, openings 410' and 430' are provided on the upper support 184 side at positions capable of connecting to the specimen introducing port 410 and the specimen suction port 430 of the sensor chip 100, and are respectively connected to the specimen, i.e., an object to be analyzed, and to the suction unit (not shown). In addition, the suction path 150 extending to the suction unit is provided on the upper support. Namely, the specimen is introduced through the opening 410', and is fed in the order of the specimen introducing port 410, the channel 450, the specimen suction port 430, the opening 430', the suction path 150, and the suction unit (not shown).

In addition, the opening 440 of the sensor chip 100, which can be used as the receptor introducing port, is sealed by the seal member 420 (rubber seal) provided on the upper support 184.

Figure 5B:
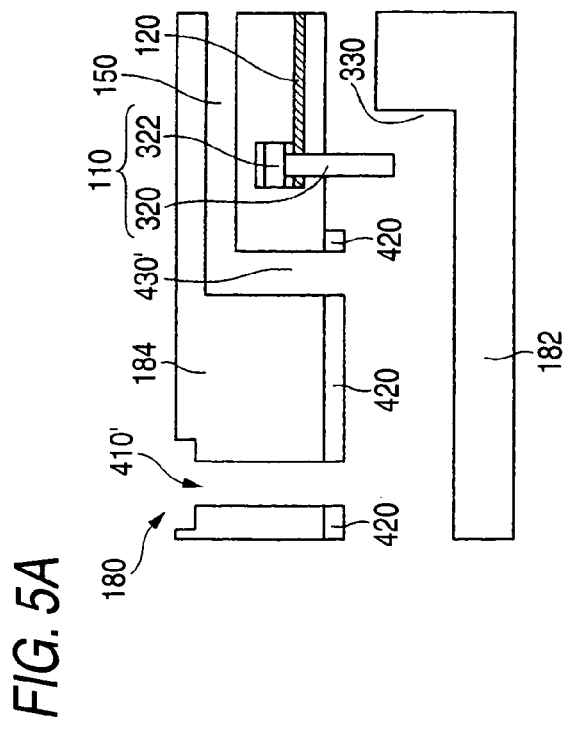
Figure 5C:
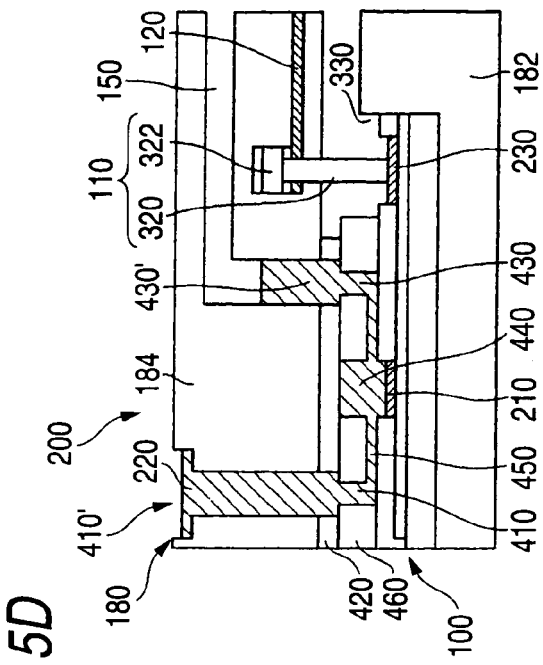

As shown in FIGS. 5B and 5C, in the same way as in the first exemplary embodiment, alignment is carried out by using the datum 330 provided on the lower support 182, and the upper support 184 is lowered toward the sensor chip side, thereby simultaneously completing the electrical connection and the sealing.

Although, in FIGS. 5A to 5D, the rubber seal is used as the seal member, the invention is not limited to the same, and the seal member is preferably formed of a flexible material but is not particularly limited.

Figure 5D:
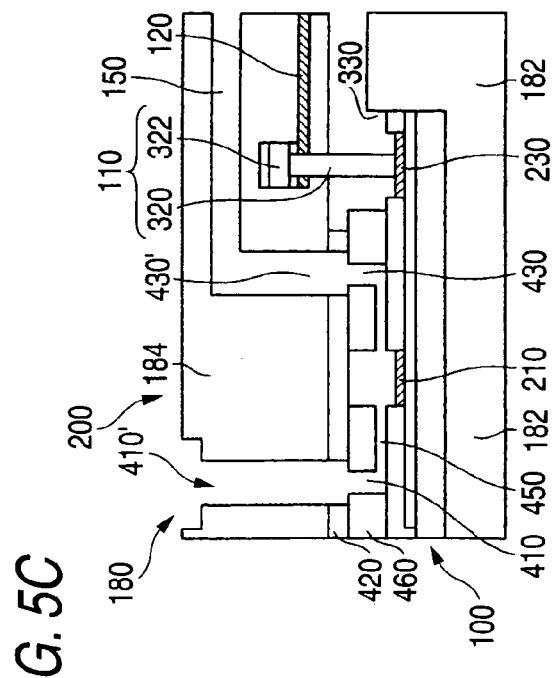

FIG. 5D shows the inspection device 200 in which the specimen has been introduced. As the specimen is sucked from the device body (substrate) side by the suction unit (not shown), the specimen supplied to the specimen introducing port is introduced into the channel substrate 460 and reaches the sensor portion 300. The channel 450 is formed by subjecting a silicon substrate or the like to microfabrication, and even a small amount of specimen with a small volume (e.g., blood) can be introduced into onto the sensor portion 300 accurately.

Figure 6A:
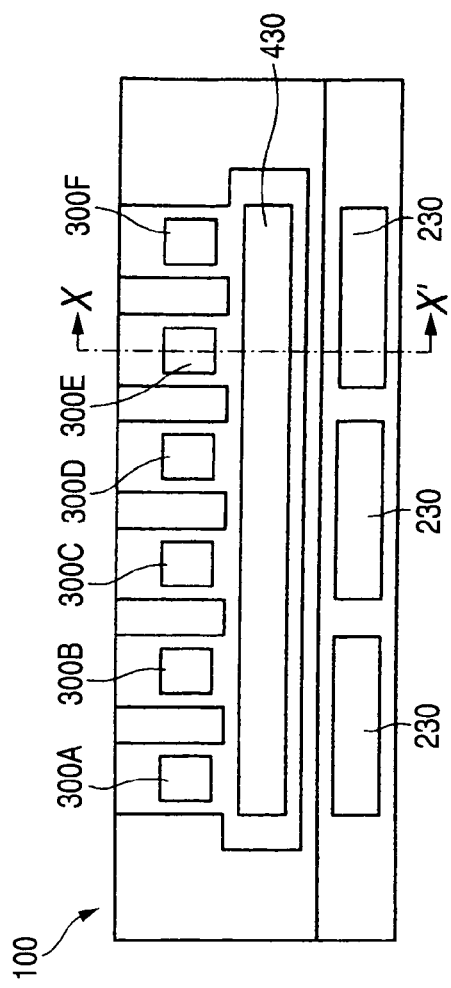
FIG. 6A is a plan view of the sensor chip 100 in accordance with a third exemplary embodiment of the invention.
Figure 6B:
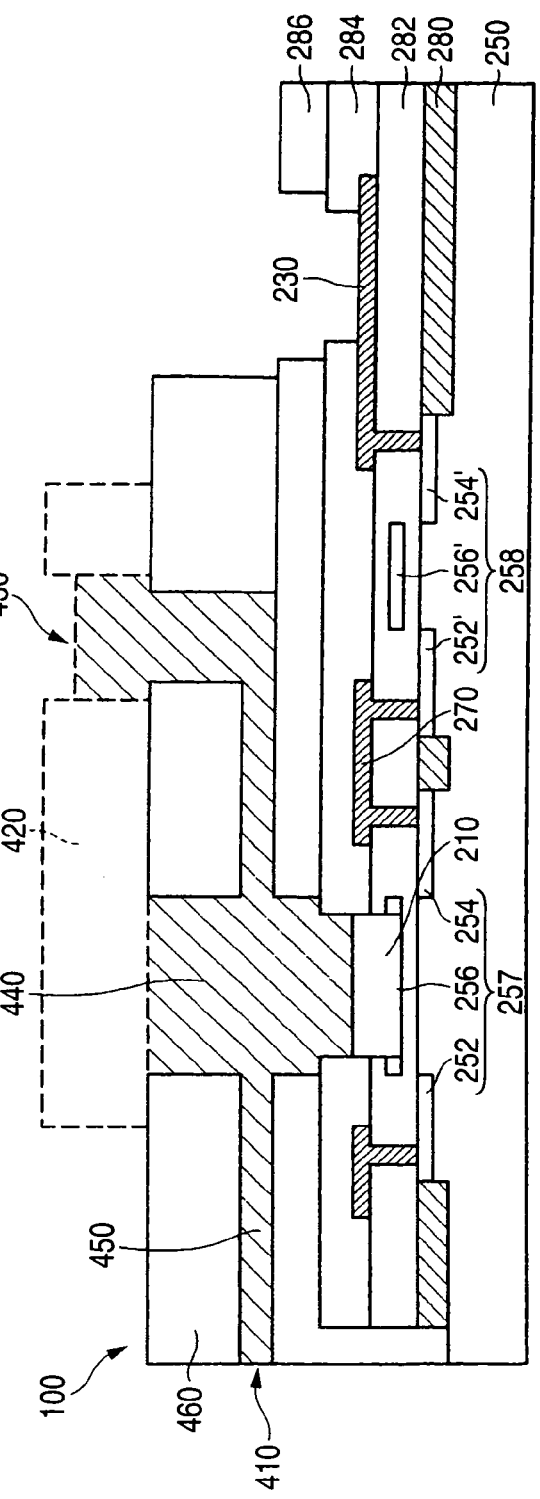
FIG. 6B is a cross-sectional view taken along line X-X' in the plan view of FIG. 6A.
Figure 7A:
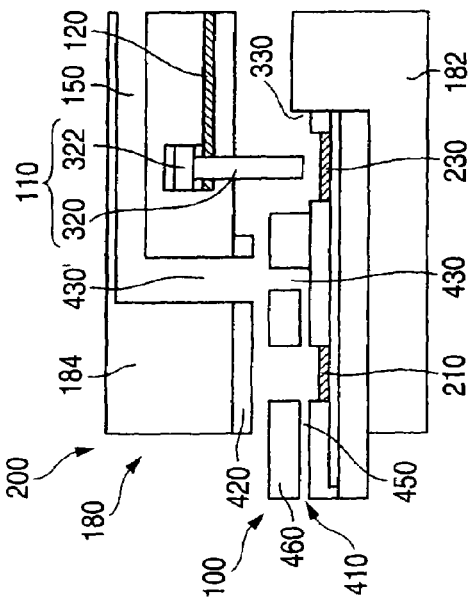
FIGS. 7A to 7D are schematic diagrams illustrating the configuration of the inspection device using the sensor chip in accordance with the third exemplary embodiment.
Figure 7B:
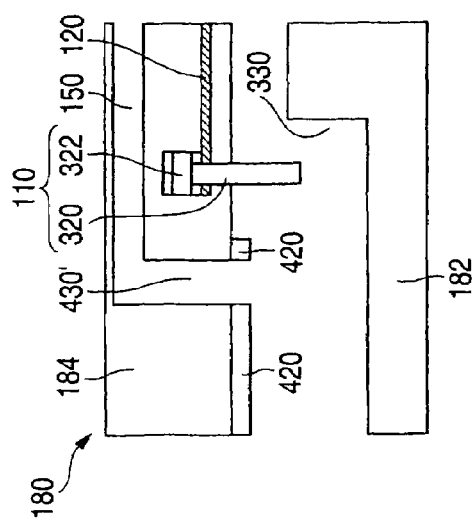
Figure 7C:
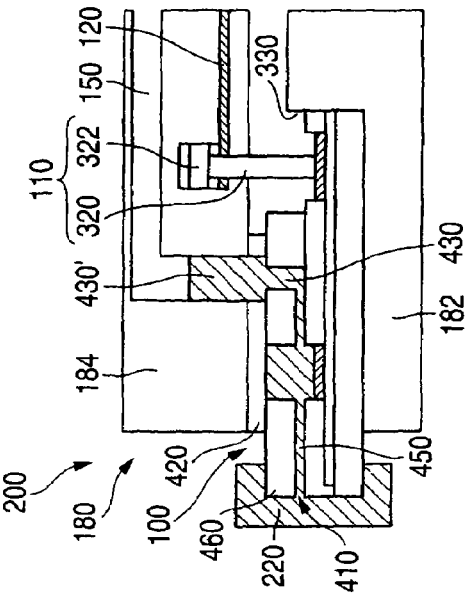
Figure 7D:
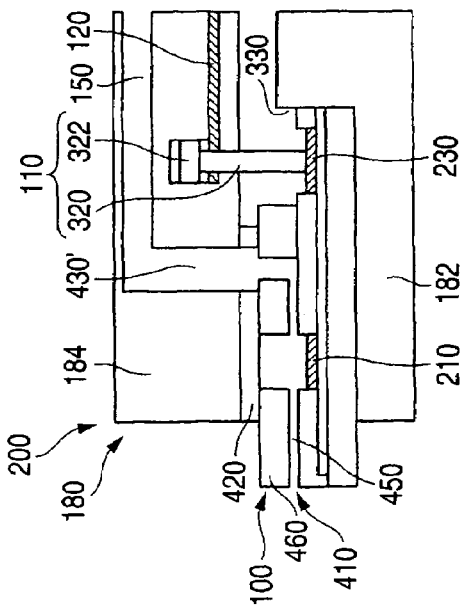

FIG. 6A is a plan view of the sensor chip 100 in accordance with a third exemplary embodiment of the invention, and FIG. 6B is a cross-sectional view taken along line X-X' in the plan view of FIG. 6A. In addition, FIGS. 7A to 7D show the configuration of the inspection device 200 using the sensor chip 100 in accordance with the third exemplary embodiment.

The third exemplary embodiment differs from the first and second exemplary embodiments in that the specimen is introduced from an end face of the sensor chip. As the specimen introducing port 410 is provided not on the upper surface of the sensor chip but on a side face thereof, the sensor chip 100 can be made further compact. Specifically, if a comparison is made between the plan view of the sensor chip shown in FIG. 4A and the plan view of the sensor chip shown in FIG. 6A, the sensor chip shown in FIG. 6A does not have the specimen introducing port on the upper surface of the sensor chip, and is made further compact in size.

In addition, the structure of the inspection device body (substrate) 180 can also be further simplified, as shown in FIGS. 7A to 7D. Namely, the upper support 184 need not be provided with the opening for introducing the specimen. Further, since the upper support 184 does not have the opening which is connectable to the specimen introducing port, the contamination of the inspection device body (substrate) from the specimen introducing port to the sensor portion due to the replacement of the sensor chip is nil, so that the cleaning of the inspection device body (substrate) is unnecessary.

Figure 8A:
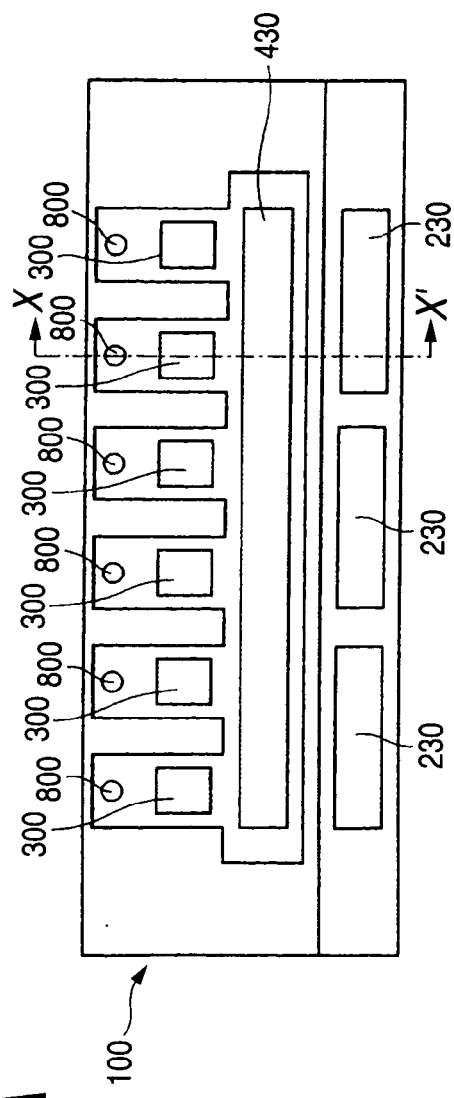
FIG. 8A is a plan view of the sensor chip in accordance with a fourth exemplary embodiment of the invention.
Figure 8B:
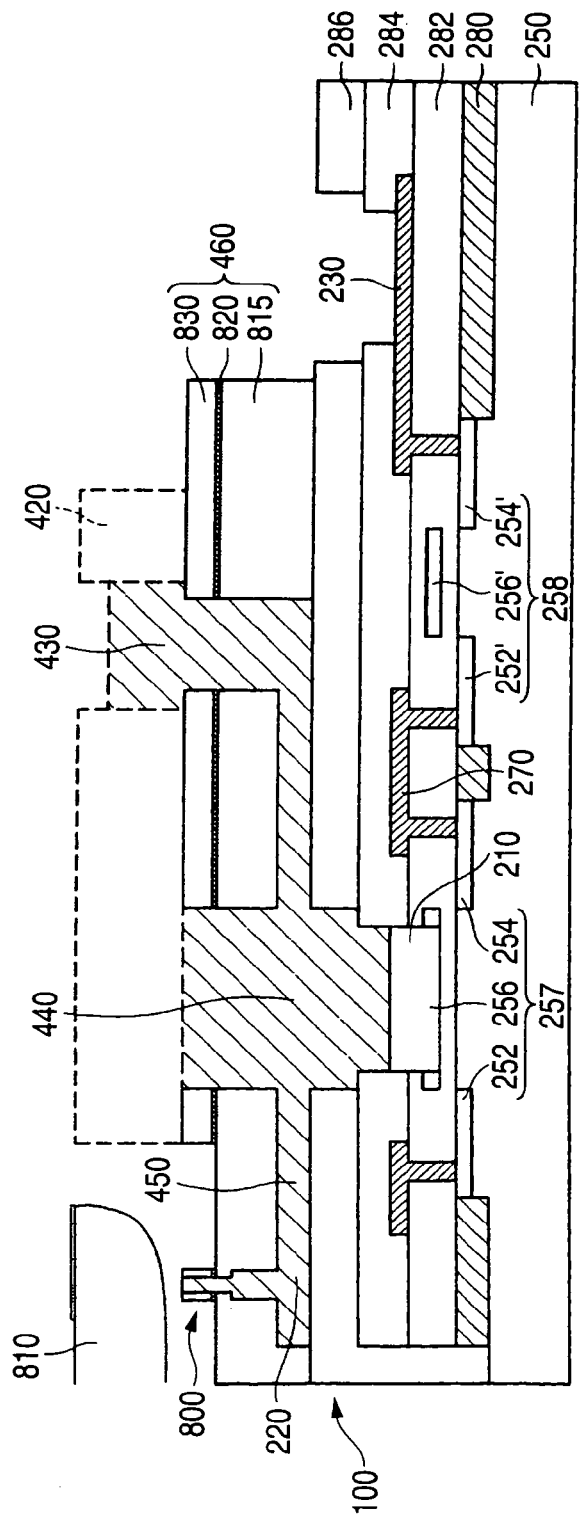
FIG. 8B is a cross-sectional view taken along line X-X' in the plan view of FIG. 8A.

FIG. 8A is a plan view of the sensor chip 100 in accordance with a fourth exemplary embodiment of the invention, and FIG. 8B is a cross-sectional view taken along line X-X' in the plan view of FIG. 8A.

In the sensor chip 100 shown in FIGS. 8A and 8B, needles 800 for blood drawing are respectively provided at the specimen introducing ports. Blood is directly drawn from a human organism by the blood drawing needle 800, and is supplied to the sensor portion 300 as the specimen 220 so as to effect analysis. The blood drawing needle should preferably be a painless needle with a diameter of 70 μm or thereabouts. A human organism (finger 810 in FIG. 8B) is pressed against and pierced by this needle portion, and as the suction unit (not shown) is operated, blood which is the specimen can be supplied therefrom to the receptor 210.

It should be noted that, in FIG. 8B, the channel substrate 460 provided with the blood drawing needle 800 can be obtained by providing an $SiO_2$ layer 820 and a Si layer 830 on a silicon substrate 815 and by subjecting them to selective etching. A description will be given later of the details.

Figure 9A:
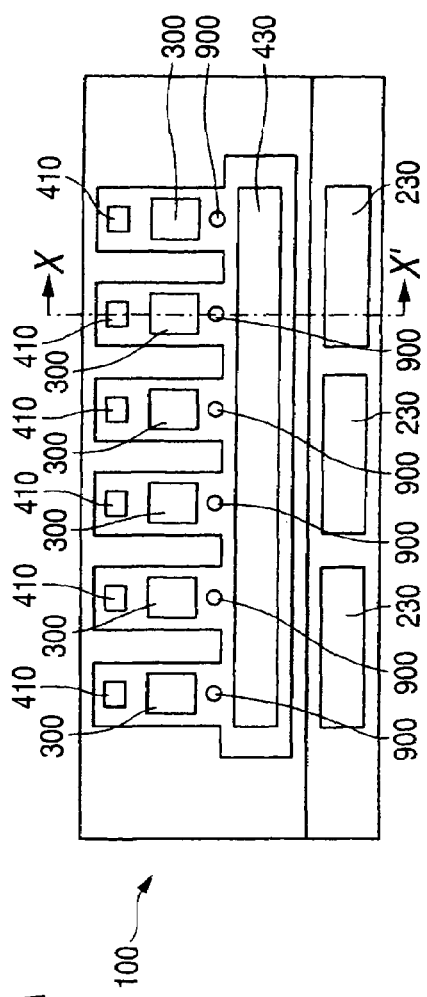
FIG. 9A is a plan view of the sensor chip in accordance with a fifth exemplary embodiment of the invention.
Figure 9B:
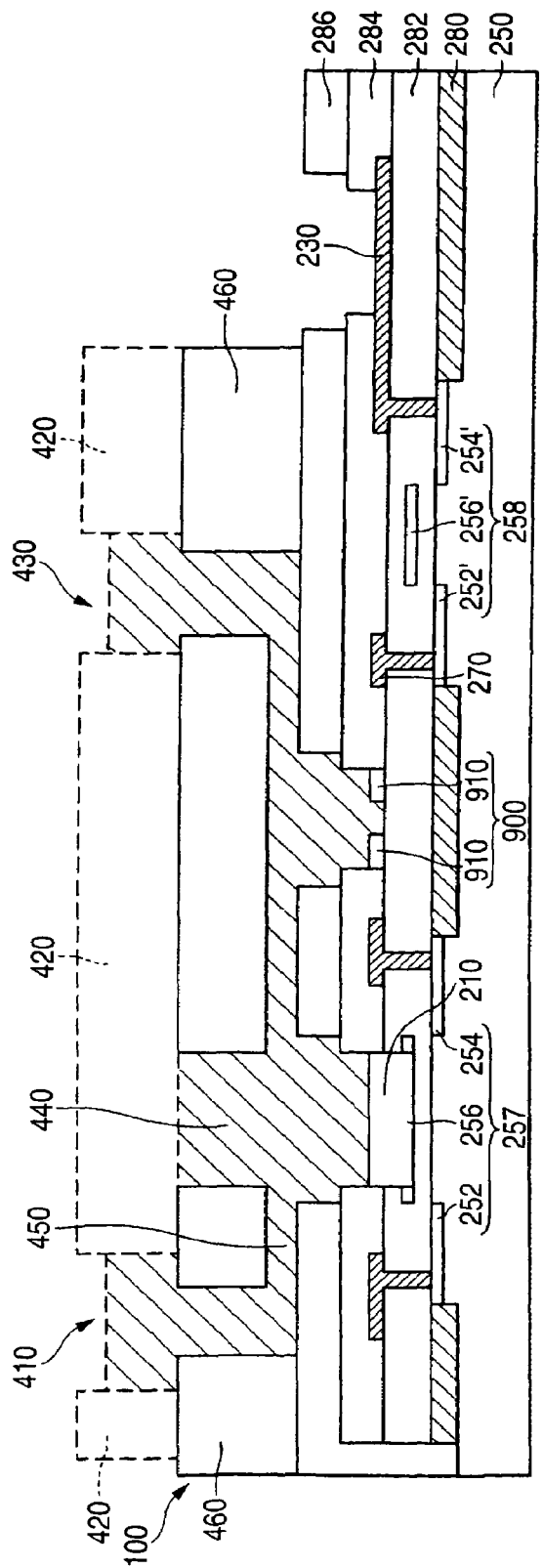
FIG. 9B is a cross-sectional view taken along line X-X' in the plan view of FIG. 9A.

FIG. 9A is a plan view of the sensor chip 100 in accordance with a fifth exemplary embodiment of the invention, and FIG. 9B is a cross-sectional view taken along line X-X' in the plan view of FIG. 9A.

In the fifth exemplary embodiment of the invention, a fluid sensor 900 is provided in the channel between the sensor chip 300 and the specimen suction port 430. When the specimen reaches this liquid sensor 900, it follows that the specimen has positively been supplied to the sensor portion 300 located on the upstream side thereof. More accurate diagnosis can be made by conducting analysis (inspection) after confirming that the specimen has been supplied.

Specifically, as this liquid sensor 900, it is possible to use, for example, a sensor of the electric conduction detection method. If a pair of conduction terminals 910 are exposed in the channel, and a specimen (liquid) is supplied therebetween, an electric current flows, thereby making it possible to confirm conduction (i.e., the presence of the liquid).

The channel substrate 460 (e.g., the Si substrate) and the inspection device body (substrate) are often opaque, and even if they are transparent, the channel 450 is infinitesimally small and is difficult to confirm visually, so that it is useful to dispose such a liquid sensor. In addition, as the suction is stopped at a stage where the presence of the specimen (liquid) has been detected, it is possible to prevent the suction of an excess amount of specimen (liquid). Namely, it is possible to reduce the amount of specimen required for analysis, and even with a small amount of specimen, analysis is made possible more reliably.

Figure 10:
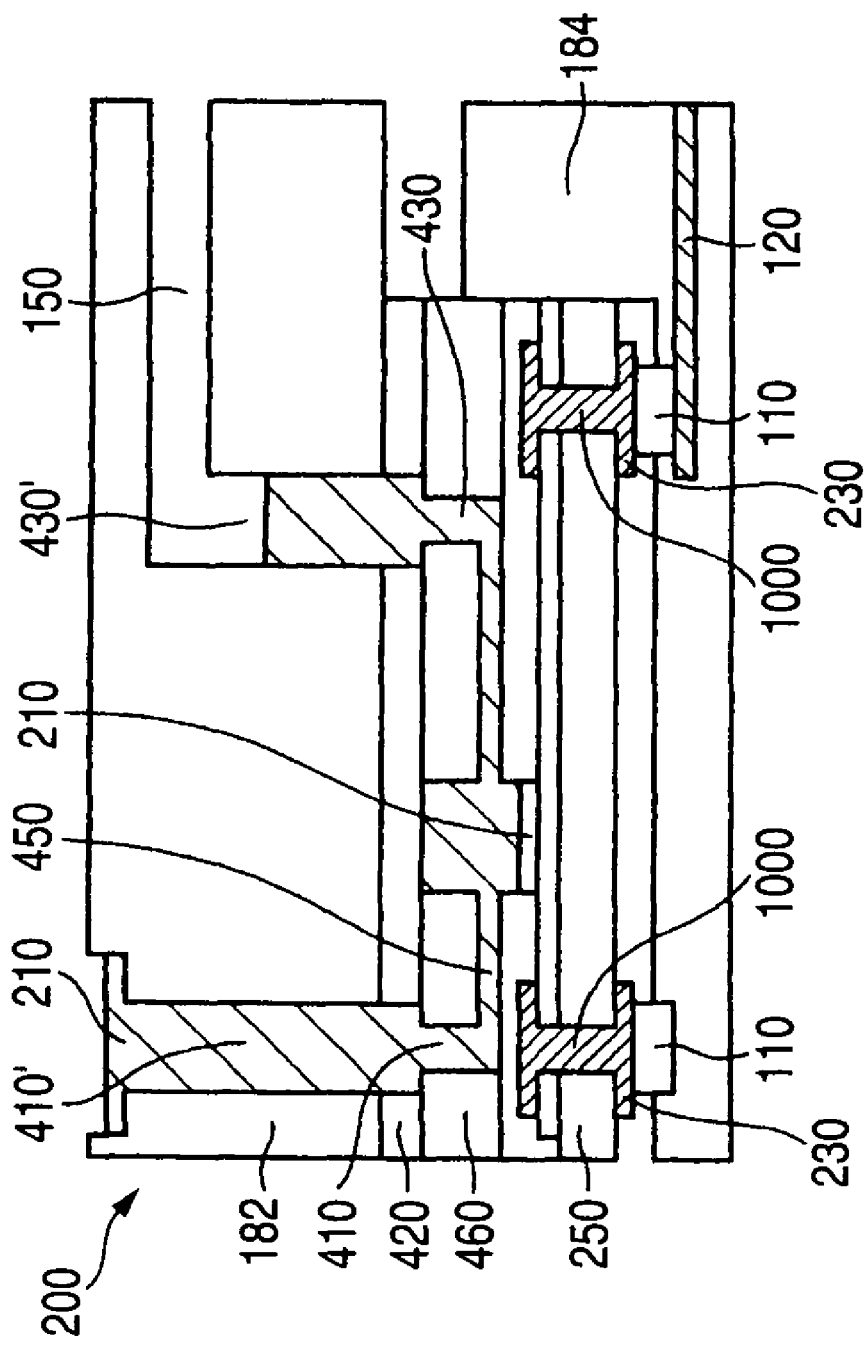
FIG. 10 is a schematic diagram illustrating the configuration of the inspection device using the sensor chip in accordance with a sixth exemplary embodiment of the invention.

FIG. 10 shows the configuration of the inspection device 200 using the sensor chip 100 in accordance with a sixth exemplary embodiment of the invention. In the sixth exemplary embodiment, the electrical connection portions 110 are provided on the reverse surface side of the sensor chip 100. Here, the electrical connection pads 230 are disposed on the reverse surface of the Si substrate 250 by providing via electrode wirings 1000 in the Si substrate 250 on the obverse surface of which semiconductor integrated circuits are formed. In addition, as shown in FIGS. 3A to 3D, the electrical connection portion 110 is preferably formed by a probe pin and a spring, or may be simply formed by an electrode and the like to allow electrical connection.

Figure 11:
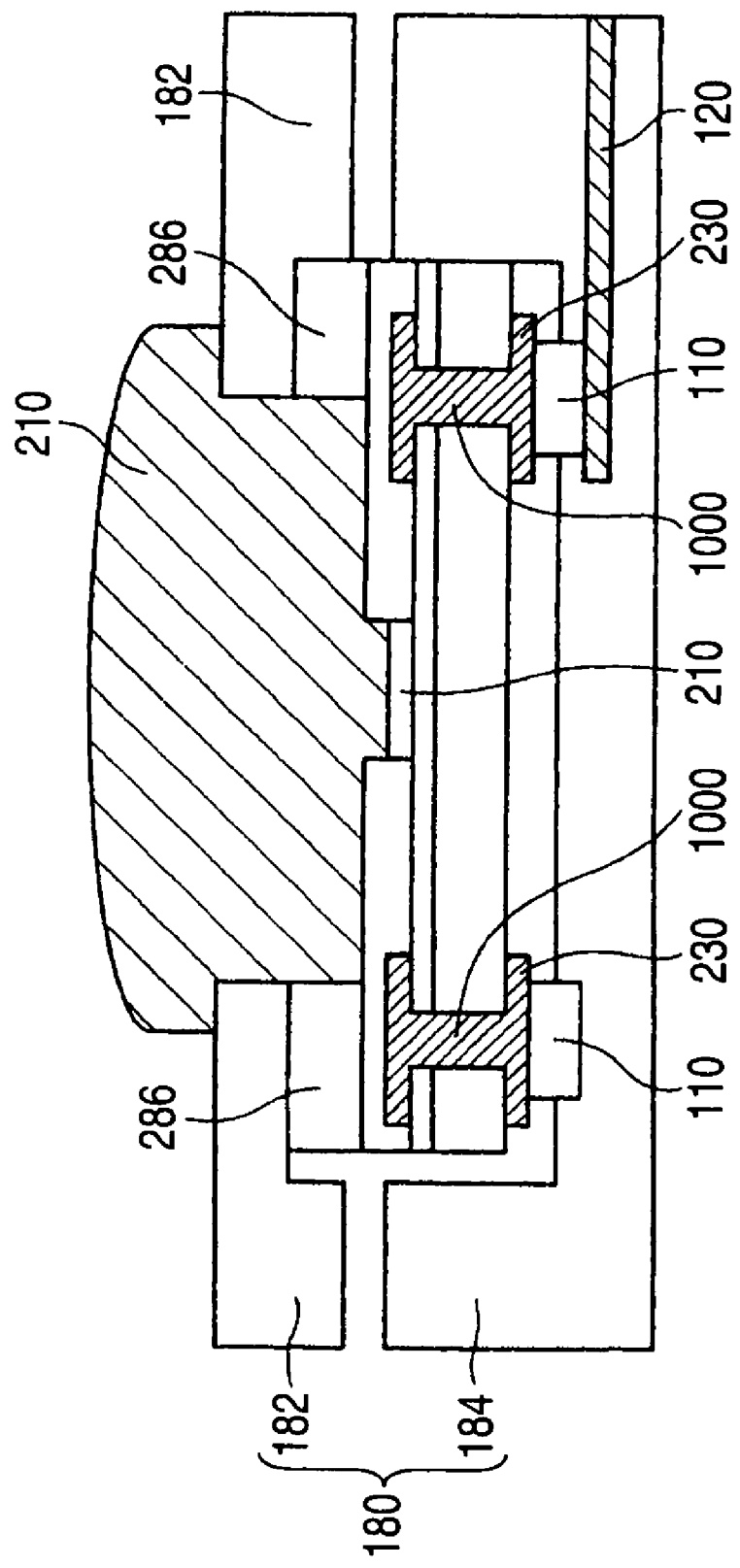
FIG. 11 is a schematic diagram illustrating the configuration of the inspection device using the sensor chip in accordance with a seventh exemplary embodiment.

FIG. 11 shows the configuration of the inspection device 200 using the sensor chip 100 in accordance with a seventh exemplary embodiment. In the seventh exemplary embodiment, since the electrical connection portion 110 is not present on the surface of contact with the specimen, so that the seal member is simplified. In addition, by omitting the channel, the inspection device body and the sensor chip can be provided with simple structures.

It should be noted that FIGS. 10 and 11 shows the semiconductor integrated circuit in a partly omitted fashion.

Figure 12A:
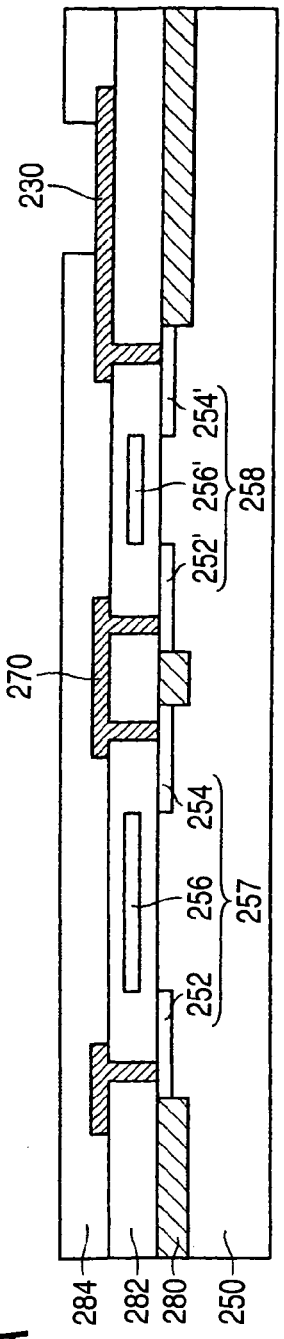
FIGS. 12A to 12C are process diagrams illustrating an example of the manufacturing process flow of a sensor substrate 1250 which can be suitably used in the invention.
Figure 12B:
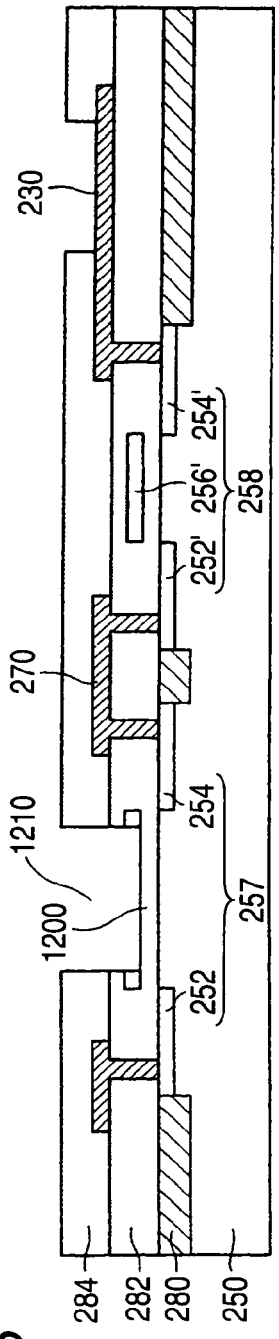
Figure 12C:
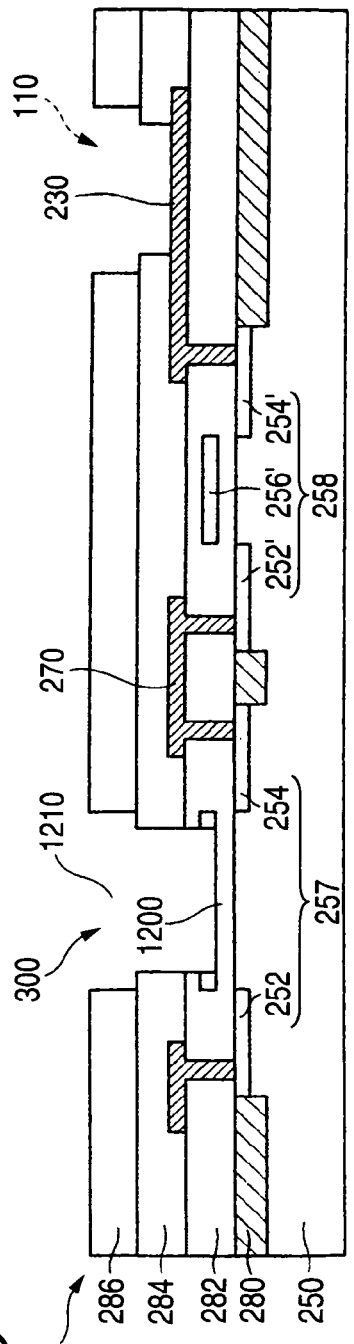

FIGS. 12A to 12C are process diagrams illustrating an example of the manufacturing process flow of a sensor substrate 1250 which can be suitably used in the invention.

As shown in FIG. 12A, an ordinary semiconductor integrated circuit is formed on the substrate 250. Subsequently, the portion of the gate 256 of the sensing transistor 257 as well as a portion of the protective film 284 thereabove are removed by photolithography and dry etching to thereby provide an opening 1210 and expose a gate insulation film 1200 (FIG. 12B). Subsequently, the polyimide film 286 serving as a bonding layer is formed. Here, the polyimide film 286 is formed by using a photosensitive polyimide through its application, exposure, and development, and portions of the polyimide film 286 at the sensor portion 300 and the electrical connection portion 110 are then removed (FIG. 12C).

FIGS. 13A to 13J are schematic process diagrams illustrating an example of the fabrication flow of the channel substrate 460 which can be suitably used in the invention. It should be noted that the fabrication flow of the channel substrate 460 in the fourth exemplary embodiment is shown here. Reference is had to FIGS. 8A and 8B as well.

Figure 13A:
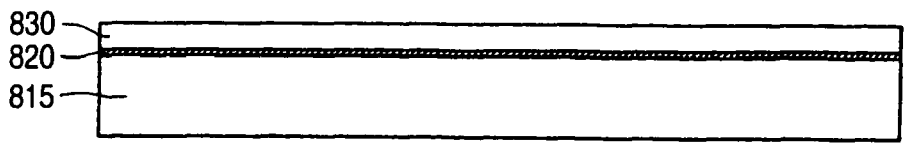
FIGS. 13A to 13J are process diagrams illustrating an example of the fabrication flow of a channel substrate which can be suitably used in the invention.

As shown in FIG. 13A, the $SiO_2$ layer is provided on the silicon substrate 815, and the Si layer 830 is further provided thereon. Here, the thicknesses of the respective layers are, for example, the silicon substrate 815: 500 μm, $SiO_2$ layer 820: 1 μm, and the Si layer 830: 250 μm or thereabouts.

Figure 13B:
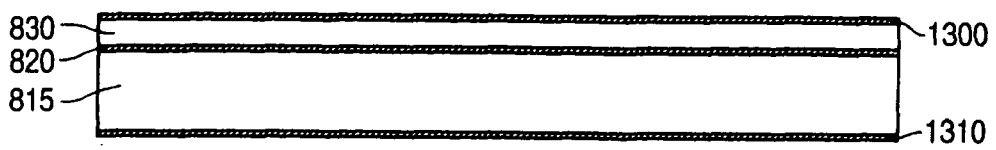

Next, the surfaces of the silicon substrate 815 and the Si layer are subjected to oxidation treatment by thermal oxidation. The oxidation conditions can be set appropriately, and by performing wet oxidation at 1000° C. for 600 minutes, it is possible to form $SiO_2$ layers 1300 and 1310 of 1 μm (FIG. 13B). Here, it is assumed that, in FIGS. 8A and 8B, the surface in contact with the seal member 420 is the obverse surface, and the surface in contact with the channel 450 is the reverse surface. Accordingly, in FIG. 13B, the obverse surface is the $SiO_2$ layer 1300, and the reverse surface is the $SiO_2$ layer 1310.

Figure 13C:
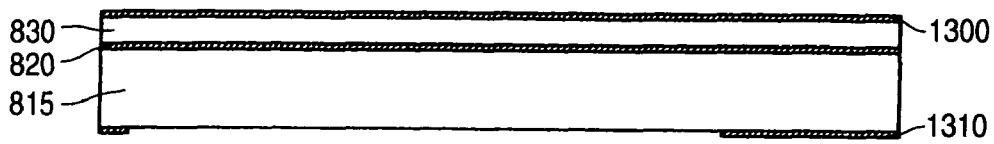

Next, a resist is applied to the $SiO_2$ layer 1310 on the reverse surface, and after its exposure and development, the $SiO_2$ layer 1310 on the reverse surface is subjected to etching by reactive ion etching (RIE) and then the resist is removed, thereby forming a patterned $SiO_2$ layer 1310 (FIG. 13C).

Figure 13D:
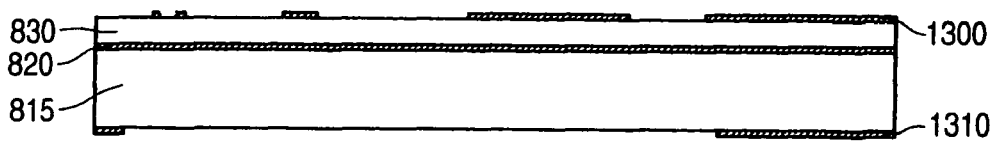

Further, the resist is similarly applied to the $SiO_2$ layer 1300 on the obverse surface, and after its exposure and development, the $SiO_2$ layer 1300 on the obverse surface is subjected to etching by RIE and then the resist is removed, thereby forming a patterned $SiO_2$ layer 1300 (FIG. 13D). It should be noted that the order of FIG. 13C and FIG. 13D is not limited to the same, and after patterning the $SiO_2$ layer 1300 on the obverse surface, the $SiO_2$ layer 1310 on the reverse surface may be patterned.

Figure 13E:
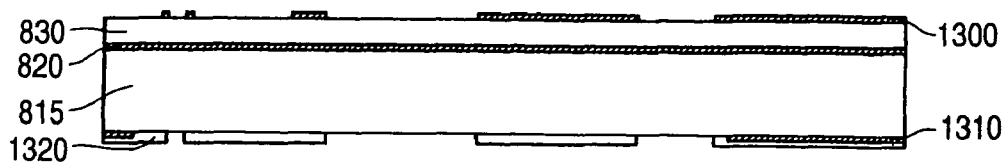
Figure 13F:
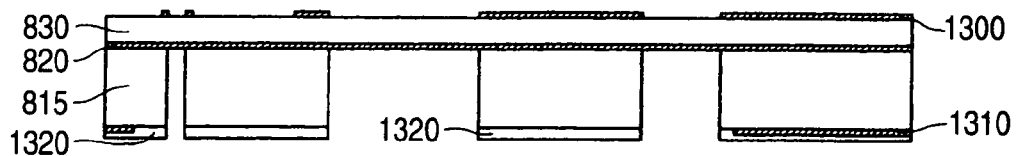
Figure 13G:
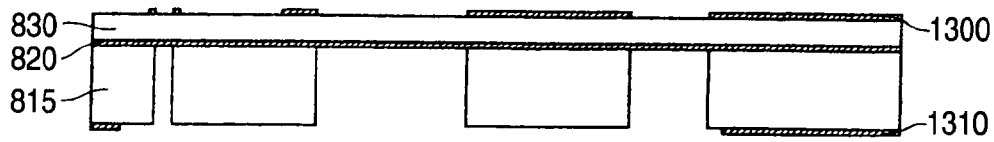

Next, the resist 1320 is formed on the reverse surface, and by its exposure and development a resist pattern is formed (FIG. 13E). Subsequently, the silicon substrate 815 is subjected to etching up to $SiO_2$ layer 820 by using the resist 1320 as a mask (FIG. 13F), thereby making it possible to obtain a patterned silicon substrate 815 (FIG. 13G).

Figure 13H:
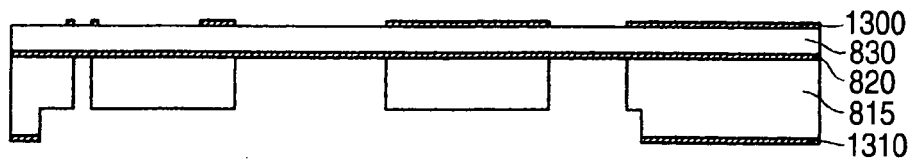
Figure 13I:
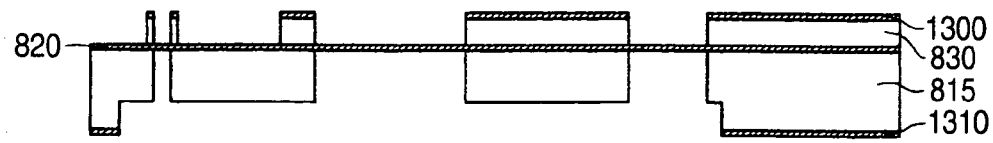
Figure 13J:
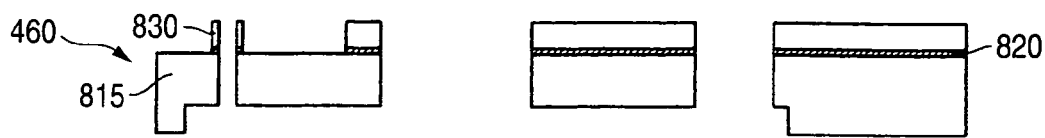

After the removal of the resist (FIG. 13G), the silicon substrate 815 is subjected to etching through RIE by using the $SiO_2$ layer 1310 on the reverse surface as a mask (FIG. 13H).

Subsequently, the Si layer 830 is subjected to etching through RIE by using the $SiO_2$ layer 1300 on the obverse surface as a mask (FIG. 13I), and portions of the $SiO_2$ layer 1300 and the $SiO_2$ layer 820 on the obverse surface are removed by HF etching, thereby making it possible to fabricate the channel substrate 460 shown in FIG. 8B.

Figure 14A:
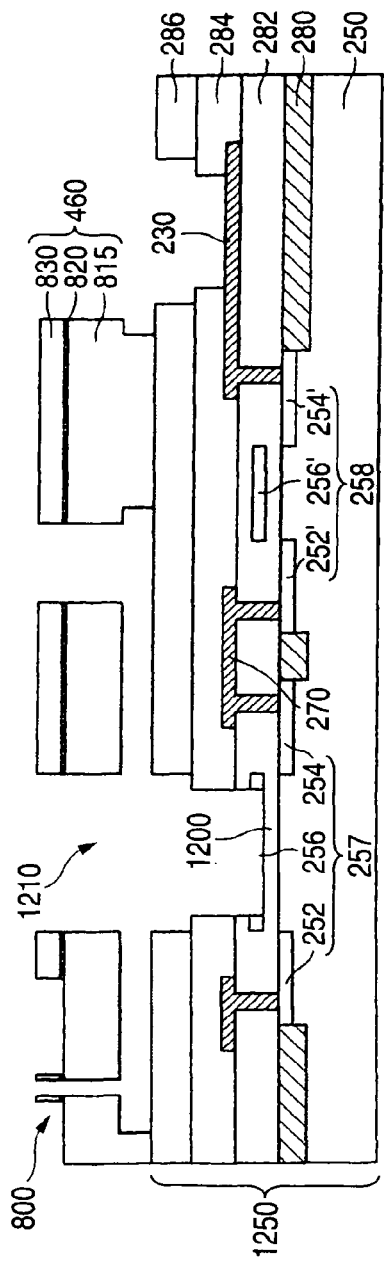
FIGS. 14A and 14B are schematic diagrams respectively illustrating processes for bonding the sensor substrate and the channel substrate and for supplying a receptor.
Figure 14B:
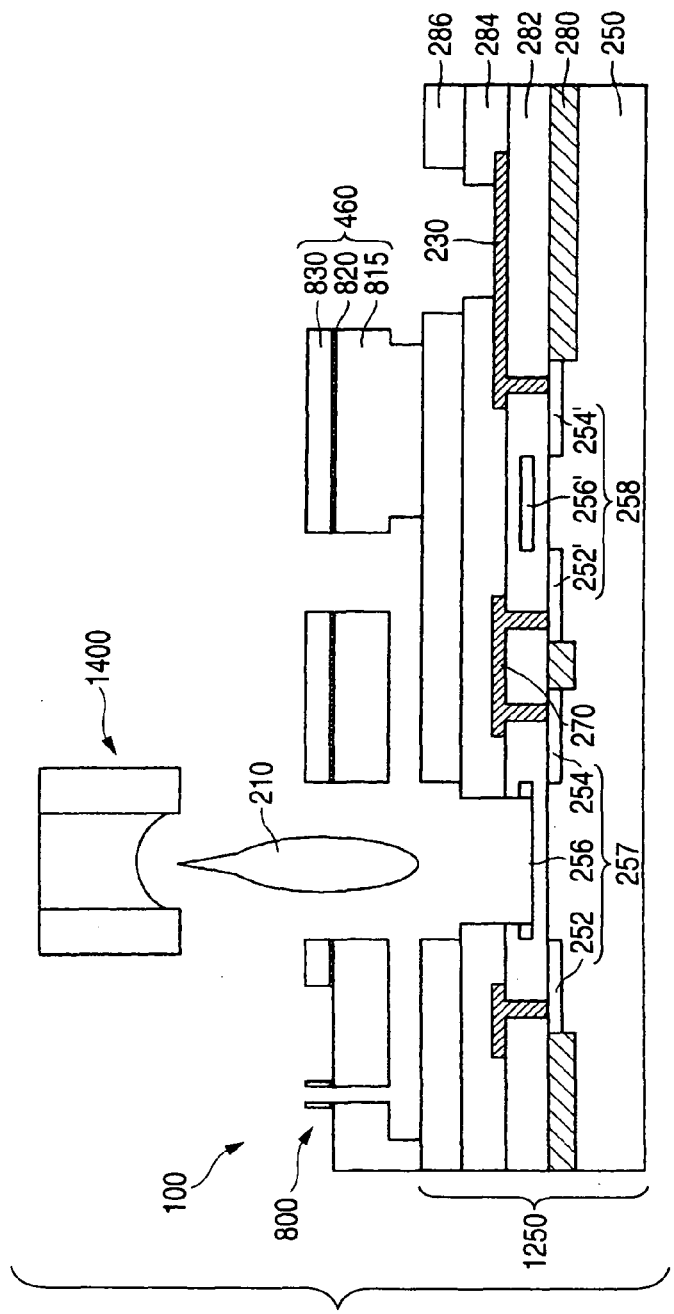

FIGS. 14A and 14B are schematic diagrams respectively illustrating processes for bonding the sensor substrate 1250 and the channel substrate 460 and for supplying the receptor 210. The channel substrate 460 is bonded by using as a bonding layer the polyimide film 286 formed on the obverse surface of the sensor substrate 1250. Although the bonding method is not particularly limited, bonding can be effected by heating in a vacuum, for example. Although the heating temperature is not particularly limited insofar as it falls within a bondable range, it is possible to cite, by way of example, heating at 300° C. to 400° C. (FIG. 14A).

Subsequently, the receptor 210 is supplied through a receptor-supplying through opening (in FIGS. 12B and 12C, this opening is shown at 1210 above the gate insulation film 1200) and onto the gate insulation film 1200 of the sensing transistor therebelow by an imparting means (shown at 1400 in FIG. 14B) based on an inkjet method or a dispensing method (FIG. 14B). These supplying methods make it possible to supply minimum necessary receptors to arbitrary locations. Since these receptors are often expensive, the amount of receptors used can be reduced by selectively supplying the receptors by the inkjet method or the dispensing method.

Furthermore, tailor-made diagnosis (inspection) is made possible as the receptors are changed in correspondence with required items of inspection.

By adopting the above-described configuration, it becomes possible to effect the supplying of the receptor as a final stage of the sensor chip fabrication process. Further, since the receptor is not affected by heat and chemical treatment in the fabrication process of the sensor chip, it is possible to avoid denaturation of the receptor due to the heat or chemical treatment.

In the invention, as receptors, it is possible to select various receptors. For instance, to allow the sensor chip to function as a pH sensor, it is possible to use an $Si_3N_4$ membrane which is an ion sensitive membrane.

The $Si_3N_4$ membrane binds to hydrogen ions ($H^+$) in the specimen. Hydrogen ions in an amount dependent on the hydrogen ion concentration in the specimen reach equilibrium in a state of being bound to the $Si_3N_4$ membrane. Meanwhile, as the source potential (substrate potential) of the ISFET, a potential of a reference electrode is imparted as a reference electrode. An ideal reference electrode has a characteristic that the potential distribution of the electrode solution interface does not change due to the kind or concentration of the solution.

If the concentration of hydrogen ions is high with respect to such a stable source electrode, the amount of hydrogen ions bound to the $Si_3N_4$ membrane increases, and the channel resistance of the ISFET declines. On the other hand, if the hydrogen iron concentration is low, the amount of hydrogen ions bound to the $Si_3N_4$ membrane decreases, and the channel resistance of the ISFET increases. Accordingly, by detecting this change, it is possible to measure the hydrogen ion concentration in the specimen.

As for these detection methods, reference can be had to JP-A-2005-207797.

In the invention, the receptor can be selected, as required. For example, a DNA sensor can also be realized by a similar structure. In the case of the DNA sensor, it is possible to cite, by way of example, a method in which a metallic layer is deposited on the gate 256 of the ISFET, and a probe DNA is adhered to the metallic layer. The material of the metallic layer is required to be a substance to which the probe DNA is easily adhered, and it is possible to cite, by way of example, such as gold. The target DNA in the specimen binds specifically to the probe DNA of such a DNA chip. The DNA has a negative charge, and as the target DNA binds specifically to the probe DNA, the potential of the ISFET changes. By making use of this characteristic, it is possible to detect the presence or absence and the concentration of the target DNA in the specimen in the same way as the above-described pH sensor.

In addition, it is also possible to detect an organic substance such as protein. In a case where the target protein has neither a positive nor a negative charge, pretreatment is carried out in advance for modifying the target protein with a charge. In a gate region to which an antigen for the target protein is adhered, if the protein in the specimen is specifically bound to the ISFET due to the antigen-antibody reaction, the gate potential of the ISFET changes. This makes it possible to effect the detection of an organic substance in the specimen.

It should be noted that the invention is not limited to the above-described exemplary embodiments, and its configuration can be modified, as required.

What is claimed is:

1. A sensor chip of an electrical signal detection type, connected to an inspection device body, the sensor chip comprising:
   a semiconductor sensing device including at least a first transistor and a second transistor, the first transistor allowing an electric charge to flow as a signal and the second transistor is connected to the first transistor with a connecting portion;
   an inter-element separation film, wherein the first transistor and the second transistor are separated by the inter-element separation film;
   a connecting member to electrically connect to the inspection device body, wherein the sensor chip is detachable with respect to the inspection device;
   a sensor portion in which a receptor is disposed;
   a substrate channel disposed on the sensor chip, the substrate channel including a material introducing port and an opening; and
   a sealing member disposed on the substrate channel so to seal the opening of the substrate channel, wherein
   the sensor portion defines an opening through which the receptor is introduced,
   the receptor is an agent that reacts physically and through contact with a material to be sensed,
   the first transistor is an ion sensitive field effect transistor,
   the material introducing port and the opening of the substrate channel are connected via a channel, and
   the opening of the substrate channel is positioned above the opening through which the receptor is introduced.

2. The sensor chip according to claim 1, further comprising:
   a specimen suction port; and
   a liquid sensor provided between the sensor portion and the specimen suction port.

3. The sensor chip according to claim 1,
   wherein the sensor chip has a plurality of receptors.

4. The sensor chip according to claim 1,
   wherein the receptor is supplied to the sensor portion by an inkjet method or a dispensing method.

5. The sensor chip according to claim 1, further comprising a needle for blood drawing.

6. An inspection device comprising:
   the sensor chip according to claim 1; and
   the inspection device body on which the sensor chip is mounted.

7. The inspection device according to claim 6, further comprising a seal member that isolates a specimen introduced into the sensor chip from an electrical connection portion between the sensor chip and the body of the inspection device.

8. The inspection device according to claim 6,
   wherein the body of the inspection device comprises a member that aligns the sensor chip.

9. The inspection device according to claim 6, further comprising an arithmetic circuit that analyzes a signal transmitted from the sensor chip.

10. The inspection device according to claim 6, further comprising a suction path and a suction unit that introduce a specimen into the sensor portion of the sensor chip.

11. The inspection device according to claim 9,
wherein the body of the inspection device comprises a probe that electrically connects the sensor chip and the arithmetic circuit.

12. The inspection device according to claim 11,
wherein the probe has a resilient function.

13. The inspection device according to claim 7,
wherein the seal member is a flexible member.

14. The inspection device according to claim 6,
wherein the inspection device is configured so that, when the sensor chip is mounted on the inspection device, (i) sealing an electrical connection portion between the sensor chip and the body of the inspection device from a specimen introduced into the sensor chip and (ii) an electrical connection between the sensor chip and the body of the inspection device are effected simultaneously.

15. The inspection device according to claim 6,
wherein the opening of the sensor portion is sealed by a flexible member provided on the body of the inspection device.

16. The inspection device according to claim 6,
wherein the receptor is supplied to the sensor chip by an inkjet method or a dispensing method.

* * * * *